United States Patent [19]

Traber

[11] Patent Number: 6,121,599
[45] Date of Patent: Sep. 19, 2000

[54] DEVICE FOR USE IN THE OPTICAL INVESTIGATION OF SURFACES

[75] Inventor: Bruno Traber, Horgen, Switzerland

[73] Assignee: Roche Diagnostics GmbH, Mannheim, Germany

[21] Appl. No.: 08/952,979

[22] PCT Filed: Jun. 5, 1996

[86] PCT No.: PCT/EP96/02445

§ 371 Date: Mar. 6, 1998

§ 102(e) Date: Mar. 6, 1998

[87] PCT Pub. No.: WO96/39621

PCT Pub. Date: Dec. 12, 1996

[30] Foreign Application Priority Data

Jun. 6, 1995 [DE] Germany .................. 195 20 606

[51] Int. Cl.[7] .................. H04N 7/18; G01N 21/00
[52] U.S. Cl. .................. 250/208.1; 250/559.05; 250/559.07; 250/559.46; 250/234; 348/79
[58] Field of Search .................. 250/208.1, 216, 250/234, 235, 559.4, 559.45, 559.46, 559.05, 559.06, 559.07, 559.08; 356/39, 244; 377/10, 11; 348/79, 80; 359/368, 391, 393

[56] References Cited

U.S. PATENT DOCUMENTS

| | | | |
|---|---|---|---|
| Re. 34,214 | 4/1993 | Carlsson et al. .................. | 348/79 |
| 4,550,417 | 10/1985 | Nunogaki et al. .................. | 377/10 |
| 4,631,581 | 12/1986 | Carlsson .................. | 348/79 |
| 4,781,464 | 11/1988 | Allington et al. .................. | 356/419 |

FOREIGN PATENT DOCUMENTS

| | | |
|---|---|---|
| 0 155 247 | 9/1985 | European Pat. Off. . |
| 0 241 904 | 10/1987 | European Pat. Off. . |

OTHER PUBLICATIONS

Journal of Chromatography, vol. 87, 1973, Amsterdam NL, pp. 67–72, M. Wenzel, "Photometrie von Dünnschichtplatten mit sichtbarem und infrarot Licht durch Leuchtdioden", No month.

*Primary Examiner*—John R Lee
*Attorney, Agent, or Firm*—Arent Fox Kintner Plotkin & Kahn PLLC

[57] ABSTRACT

A device for optical investigation of a microscope slide includes a support, and a microscope slide holder fixedly attached to the support. A holder unit is attached to the support with at least one spacer unit. The at least one spacer unit enables relative movement between the holder unit and the support. A line sensor is attached to the holder unit, and includes a plurality of sensors arranged in a row. An illuminating device is provided for illuminating a microscope slide disposed on the microscope slide holder. A lens system is attached to the holder unit, and generates an image on the line sensor of at least a part of the microscope slide. A drive is provided for moving the holder unit substantially vertically relative to the sensors of the line sensor.

49 Claims, 4 Drawing Sheets

DEVICE FOR USE IN THE OPTICAL INVESTIGATION OF SURFACES

BACKGROUND OF THE INVENTION

1. Field of the Invention

Subject matter of the invention is a device for use in the optical investigation of surfaces, especially microscope slides. The device contains a support to which a microscope slide holder is attached, and a holder that is attached to the support by means of at least one spacer unit. Attached to said holder is a line sensor in which numerous sensors are arranged in a row, and a lens system that forms an image of the microscope slide or a part of the microscope slide on the line sensor. The device also contains an illuminating device for illuminating the microscope slide and a drive for moving the holder basically vertically to the row of sensors in the line sensor by bending, tilting or pivoting the at least one spacer unit.

2. Description of the Related Art

In general, automated devices for investigating surfaces and microscope slides are based on a video system in which an image of the surface is projected onto a two-dimensional CCD array. The price of two-dimensional CCD arrays for use in video cameras has dropped dramatically in recent years. However, such CCD arrays that are common in the prior art are suitable for use in microscopic analysis only to a certain extent because they have a relatively small number of sensors and a relatively high rate of defective sensor elements. While the malfunction of individual pixels can be tolerated in inexpensive video cameras, these arrays are less suitable for use in microscopic analysis. CCD arrays with sufficiently high resolution and very low error rates are still very expensive and therefore not suitable for use in building a system for use in doctors offices and smaller laboratories.

An apparatus for counting microparticles is described in U.S. Pat. No. 4,550,417 in which an microscope slide is moved over a line sensor. In this method, the microscope slide is placed in a special holder that is moved by a linear drive. The linear drive shown in FIG. 4 comprises a synchronous motor that moves the sample carrier at a constant speed against the force of a return spring. To achieve the high level of precision necessary, the forces holding the sample carrier must be much greater than the friction forces produced when the sample carrier is moved. Accordingly, the system described here is equipped with a very strong motor and a correspondingly strong return spring. A further disadvantage of this apparatus is the fact that the sample is moved; the accelerative forces of the drive and shaking motions that are created when the sample carrier is transported cause the particles to be detected to move. This impairs the reliability of the counting and makes it difficult to identify and classify particles that are found using the sensor signals. Moreover, the apparatus described here uses a fixed light source to illuminate the sample carrier. This is a disadvantage, because the entire area that is observed must be illuminated homogeneously. As a result, the costly and energy-intensive method of illumination shown in FIG. 3 is required. To prevent the sample from being warmed by the light source, the light source is positioned away from the sample, and the light is directed by means of a reflecting mirror.

SUMMARY OF THE INVENTION

The object of the invention was to provide a simple yet inexpensive system for use in the optical investigation of surfaces that works with high resolution. Yet another task of the invention was to propose a device that prevents samples located on microscope slides from being moved. Yet another object of the invention was to provide precise transport of a line sensor over a surface using a mechanically simple and inexpensive system.

Subject matter of the invention is a device for use in the optical investigation of an microscope slide comprising a support to which an microscope slide holder is attached, a holder that is attached to the support by means of at least one spacer unit.

a line sensor attached to the holder in which numerous sensors are arranged in a row, a lens system attached to the holder that forms an image of the microscope slide or part of the microscope slide on the line sensor, an illuminating device for illuminating the microscope slide, and a drive for moving the holder basically vertically to the row of sensors of the line sensor by bending, tilting or pivoting the at least one spacer unit.

The device according to the invention is used for the optical investigation of an microscope slide. Optical investigation within the context of this invention is understood to mean that radiation that is transmitted by the microscope slide or that is reflected back by the microscope slide is evaluated. The term optical is understood to not be limited to visible light, but also includes radiation in the infrared and ultraviolet portion of the spectrum. Fluorescence measurements can also be performed using the apparatus according to the invention. The sample is usually first stained with a fluorescent dye and the sample located on the microscope slide is illuminated with a radiation that excites fluorescence. To separate fluorescent radiation from background radiation, it is especially advantageous with this measurement method to provide a filter in front of the line sensor, in the path of the radiation.

The term microscope slide in the context of the invention is understood to mean microscope slides in particular that are used in the prior art to investigate liquid samples. Moreover, microscope slides are also understood to mean diagnostic test elements, however, in which a sample— usually a bodily fluid—is applied to the test element and a reaction of the sample with the test element is investigated. The invention is especially suited for use in the investigation of diagnostic test elements that are accessible to a transmission measurement. Test elements can also be evaluated that are basically impermeable to radiation. Devices for use in the evaluation of diagnostic test elements according to the invention are especially advantageous if the test elements deliver a measured signal that is resolved in the plane, as is the case, for instance, with chromatography strips or test strips with different zones located very close to each other.

An important aspect of the invention lies in the fact that the microscope slide on which the sample is located is fixed in space during the investigation and does not move. This prevents the microscope slide from being shaken and the sample from being moved. Accordingly, the device has an microscope slide that is attached to a support. The support is fixed in space during the measurement, but it is transportable.

In a further embodiment of the invention, the system comprising the line sensor, lens system and illumination is fixed in space and the microscope slide is moved. According to the invention, the microscope slide is located inside a holder that is connected with the support by means of a spacer unit. The holder is moved basically vertically to the row of sensors in the line sensor by bending, tilting or pivoting the at least one spacer unit.

The microscope slide holder can be realized, for instance, by the mechanical stage of a traditional microscope. It is more advantageous, however, for the holder to be adapted for a specific type of microscope slide that is used with the device according to the invention. The microscope slide holder is preferably designed so that an microscope slide can be inserted into it, and the microscope slide is held and positioned in its determination position.

Moreover, the microscope slide holder should have a plane surface to support the microscope slide and a pressing device for the microscope slide to ensure that the evaluation zone of the microscope slide is located at a defined distance from the lens system of the device. The microscope slide can also have guide rails for instance, into which the microscope slide is inserted, with a defined distance set between the microscope slide and lens system.

Another important aspect of this invention is a holder to which a line sensor and a lens system are attached. The holder is made of a rigid material in order to ensure that a defined distance is maintained between the line sensor and lens system. The holder is attached to the support by at least one spacer unit. This type of holder is an advantageous aspect of the invention because it makes it possible to move the holder precisely and therefore arrange the line sensor and lens system in the space with a minimum of mechanical effort. If the individual components are attached to the spacer unit directly, a separate holder can be eliminated.

The at least one spacer unit is designed so that it can be bent, tilted or pivoted. For instance, the spacer unit can be attached to the support by means of a hinge so that it can be moved on the axis of the hinge. The hinge axis is designed so that the line sensor is pivoted within a plane that is parallel to the plane of investigation. For numerous applications the object will be to keep the distance between the line sensor and plane of investigation constant. Accordingly, it must be certain that the hinge axis is as vertical to the plane of investigation as possible. Moreover, the hinge should have as little play as possible and the spacer unit should be so mechanically stable that the chance of it being bent in the direction of the plane of investigation is minimal. Suitable hinges according to this invention are not only the usual hinges in which a pin is stuck in a tube or a rod is inserted into bore holes in the support and the spacer unit, but also the band and film hinges known from plastics engineering.

In an especially preferred variant of the device, a flexible spacer unit is used that is attached to the support. Since the spacer unit can be bent, the end of the spacer unit that is opposite the support, or the holder attached to this end can be moved parallel to the plane of investigation. The stiffness in the material from which the spacer unit is made largely prevents it from being bent vertically to the plane of investigation. As an advantage, the spacer unit has the elasticity necessary in the desired direction of bending that allows any bending to be reversed.

A flexible spacer unit can comprise a leaf spring, for instance. Suitable spring materials are elastic steel plates or plastic plates. The elastic force of the spacer unit can be adjusted by means of its length, thickness, surface and material. A plate is preferably selected as the spacer unit that, due to its width, creates a space of many centimeters between the support and the holder. The spacer unit is usually many centimeters long as well and is preferably longer than the distance between the line sensor and lens system. When the spacer unit is properly attached to the support and the holder, its length ensures that the holder can be moved over the plane of investigation by bending the spacer unit(s) without tilting the optical device away from the support. By using spacer units, which withstand shear forces without bending, one can avoid a parallel displacement from the support and holder in the direction of the optical axis, or even tilting altogether. Using plate-shaped spacer units is a simple way to guarantee that these situations will not happen. The characteristics of the spacer unit described are important because they ensure that the assembly of line sensor and lens system can be swung over the plane of the microscope slide at a constant distance. In an especially simple embodiment of the invention, the line sensor and lens system can also be attached directly to the spacer unit. In this case, the spacer unit also functions as the holder.

The holder is preferably attached to the support by means of two spacer units that are separated from each other. The support and holder are moved towards each other like parallelograms by moving the holder by bending, tilting or pivoting the spacer unit. Tilting the line sensor can be avoided by using two spacer units. If spacer units are used that are attached to the support by means of hinges, it is preferable for the spacer unit to be mechanically attached to the holder by means of hinges as well. Flexible spacer units are even preferred in the variant of the device that uses two spacer units that are separated from each other.

It is also advantageous for the invention if the support, holder and two spacer units form a tower with each other that is closed to the outside in four special directions. This design reduces the amount of extraneous light that penetrates the optics.

If necessary, the elastic force of the flexible spacer units can also be varied by changing the rigid materials attached to them and by exactly defining and limiting the bendable regions of the spacer units. Experiments have shown that an elastic force of between 5 and 10 g/mm for the spacer units is especially advantageous. In designs in which the holder is connected to the support by means of two or more spacer units, the advantageous range of elastic force described is based on the total of elastic forces created by all of the spacer units present.

The embodiments of moveable spacer units described can be used in similar fashion for the second embodiment in which the line sensor, lens system and illuminating device are attached rigidly to a support, and the microscope slide is located in a holder that is connected with the support by means of a spacer unit.

A further important element of devices according to the invention is a line sensor attached to the holder. Line sensors are sensors in which numerous individual sensors are arranged closely together in a row. CCD arrays are especially common in the prior art. To ensure the high resolution needed to investigate surfaces for a representative area of the surface to be investigated, sensors with at least 500 and, even better, more than 1000 individual sensors should be used. Due to the fact that these types of sensors are used in many different applications, e.g. in fax machines and scanners, sensors are already available with 10,000 individual sensors arranged in a row, for instance, at relatively low prices. A line sensor to be used with this invention should have a broad-banded sensitivity in at least one part of the visible spectrum. The sensor needs sufficient sensitivity at least in the range of illumination.

In special cases it can be an advantage for the sensor to have many rows of sensor elements, as is the case with the TCD 1250 D sensor from Toshiba, for instance. A sensor like this can be used, for instance, when the mechanically feasible step width is less than the desired resolution of the surface. When a multi-rowed sensor is used, many lines of the surface can be scanned with each mechanical step. A further advantage of a two- or multi-rowed sensor is the fact that results obtained with one sensor line can be checked using an additional sensor line.

A device according to the invention also has a lens system that is attached to the holder. This lens system usually comprises many lenses connected in a series that form an objective. Since the image of a narrow strip of a surface is formed on a line sensor in the device according to this invention, the lenses used in the lens system are preferably cylindrical in shape. The lens system is rigidly attached to the holder so that an image of the surface is formed on the line sensor in an exactly prescribed enlargement. For applications in particular in which the exact distance between the surface to be investigated and the lens system is not known or cannot be determined, it is advantageous to use a lens system that can be focussed. Depending on the application desired, a lens system can be selected that enlarges or reduces. An enlarging lens system is usually selected for use in the optical investigation of microscope slides because a resolution of a 1 $\mu$m area is desired to study cells. The individual sensors of common line sensors are 10 $\mu$m×10 $\mu$m in size, however. This means that an enlarging lens system is needed to achieve the desired resolution.

Proper illumination of the surface to be investigated has a strong influence on the quality of the image obtained. The top of light-impermeable samples can be exposed to light so that the reflected light is captured for evaluation. It is advantageous to select a transmitted-light device to investigate light-permeable samples such as microscope slides. Illuminating devices with continuous light sources are suitable in principle, as described in U.S. Pat. No. 4,550,417. It has been proven to be an advantage according to the invention, however, to use light diodes to illuminate the sample. Light diodes have the advantage of releasing only small quantities of heat and can therefore be placed close to the sample without warming it. Warming the sample would be disadvantageous, especially when investigating microscope slides, because evaporation of sample fluid can change the concentration or even form air bubbles in the space under investigation.

It is especially advantageous to arrange many monochromatic light diodes in one row for illumination. Arranging the light diodes in a row ensures that the strip-shaped area of the sample being investigated is illuminated relatively homogeneously. The use of monochromatic light diodes has proven to be superior to a white light source. The reason for this has not been definitively explained; however, it is possible that the influence of extraneous light on the measurement has fewer effects when relatively narrow-banded light sources are used.

The homogeneity of the illumination can also be improved by installing a matt screen above the row of light diodes.

It is also advantagous to expand the illuminating device by using two or more rows of monochromatic light diodes that can be selectively activated if necessary. For certain tasks such as differentiating red and white blood cells, it has proven to be advantageous to perform the optical investigation twice at different wavelengths in order to derive inferences from the difference between the two digital images. While a static illuminating device is proposed in the prior art (U.S. Pat. No. 4,550,417), it has proven to be advantageous according to the invention to attach the illuminating device to the holder as well. The illuminating device is therefore located in the same position with regard for the lens system and line sensor in every phase of the measurement. This way it can be ensured that all areas of the sample are investigated under the same illumination conditions.

A drive is used to move the lens system and the line sensor over the area of the surface to be investigated or to move the microscope slide holder in the second embodiment of the invention. The drive comprises a step motor with a threaded rod or a spindel mounted to its axis. The spindle turns in a threaded section (nut) that is attached to the holder. In the resting position of the spacer unit, it is advantageous for the spindle to be vertical to the plane of the flexible spacer unit. Since the holder tilts in relation to the spindle as the spacer unit(s) move(s), the nut must be attached to the holder in such a way that it can change direction slightly while guiding the holder with as little play as possible. This can be achieved by positioning the nut on a plate that is attached to the holder. With this type of holder, the spindle axis also moves minimally within the space, which makes it necessary for the spindle and the motor to be supported properly. When used for the optical investigation of microscope slides, the necessary shifting of the spacer unit is minimal, so that the direction of the spacer unit with regard to the spindle axis deviate from vertical (90°) by only a few degrees. The deviation from vertical is typically less than ten degrees. With the design according to the invention, the line sensor is moved basically vertically to the row of sensors.

To decrease the amount of mechanical play between the threaded rod and the nut when the drive is activated, the holder can be preloaded by means of a spring in a direction that is parallel to the axis of the threaded rod. If the optical evaluation is performed in an area in which the spacer units are under bending stress, an additional spring can be eliminated, if necessary.

With the design described it is possible to use a relatively weak drive motor with a torque of between 100 and 500 g·cm. Experiments have shown that accuracies in the step width of 0.5 $\mu$m can be achieved even with a mechanically very simple spindle support.

If surfaces are investigated using the device described, signals are obtained on the line sensor that are processed further for evaluation. With the common monochromatic sensor elements, a digital value that represents a gray value is obtained for each sensor element of the line sensor. An evaluation can be performed based on the gray values that is more accurate than the resolution of individual sensor elements.

The evaluation of sensor signals obtained by scanning the surface can be performed by a computer using a known method. To increase the precision and accuracy of the evaluation, it is advantageous to first perform a measurement using the line sensor in an area that contains no sample. Deviations in the sensitivity of the sensor elements and inhomogeneities in the illumination and the lens system can be offset by taking these reference lines into account.

Evaluation results obtained with devices according to the invention are usually images that are evaluated by a computer using the appropriate software in order to determine the number of cells of a certain quantity, for instance. Moreover, it is possible to search specifically for rare cell types such as cylinders in the image, and to display these sections of the image on a monitor for the operator to view. In addition to image evaluation, the devices according to the invention can also measure concentration by means of transmission or remission measurement, however. A concentration measurement of this type can be important in the evaluation of blood samples, for instance, when erythrocytes are lysed. The staining present in the sample medium after this lysis can be used to deduce the quantity of erythrocytes present. Moreover, a concentration determination using transmission or remission measurement can be used advantageously to evaluate diagnostic test elements.

The evaluation results and, if necessary, an image of the scanned surface can be displayed on a monitor. The operator can initiate the measurement on a computer terminal. The individual steps that the drive performs to scan the surface can be controlled either using a motor control or the computer.

A further aspect of the invention concerns a device for the optical investigation of surfaces, comprising a line sensor in which numerous sensors are arranged in a row,
  a lens system for forming the image of the surface or a part of the surface on the line sensor,
  a holder to which the lens system and the line sensor are attached,
  a support to which the holder is attached by means of at least one spacer unit,
  a drive that moves the holder basically vertically to the row of sensors of the line sensor by means of bending, tilting or pivoting the at least one spacer unit.

The device described can be used, for instance, to investigate surfaces of diagnostic test elements, semiconductive materials, polished surfaces, tissue or skin surfaces. The function and design of many elements of this device correspond to that of elements of the device for use in the optical investigation of microscope slides. The difference is that the device for use in the optical investigation of surfaces does not necessarily have a holder for an microscope slide or the like. To investigate surfaces, the device support can be placed on the surface. The support therefore preferably has elements with which it can be placed on the surface to be investigated. In many of the applications named, it will be advantageous to expose the surface to be investigated to light from the top, and to evaluate the reflected light. This can be accomplished using an illuminating device attached to the support, for instance. With this embodiment of the invention it is also advantageous to attach the illuminating device to the holder so that it is moved as well when the surface is scanned. Unless specified in greater detail for this and subsequent embodiments of the invention, the above descriptions of components and the way they work together shall apply.

To make the device described accessible for a wide variety of uses, the support can be height-adjustable. It is also advantageous to equip the lens system with height adjusting mechanism as well, so that the surface can be brought into focus.

The invention also includes a device for use in the optical investigation of microscope slides, comprising a support to which an microscope slide holder is attached by means of at least one spacer unit,
  a line sensor attached to the support in which numerous sensors are arranged in a row,
  a lens system attached to the support that forms the image of the microscope slide or a part of the microscope slide on the line sensor,
  an illuminating device for illuminating the microscope slide, and
  a drive for moving the microscope slide holder basically vertically to the row of sensors of the line sensor by bending, tilting or pivoting the at least one spacer unit.

In the embodiment described, the sensor, lens system and illuminating device are attached rigidly to the support. The microscope slide is located in an microscope slide holder that is attached to the support by means of at least one spacer unit In contrast to the embodiments described above, the microscope slide holder and, therefore, the microscope slide, are moved in this case. This embodiment, with its bending, tilting or pivoting of the spacer unit according to the invention, has the advantage over the prior art described in U.S. Pat. No. 4,550,417 that a high precision of movement can be achieved with a simple mechanical arrangement.

The invention also includes a device for use in the optical investigation of microscope slides, comprising a holder to which a line sensor, a lens system and an illumination system are attached,
  a support to which a microscope slide holder is attached,
  a drive that moves the holder in relation to the support in such a way that the distance from the line sensor, lens system and illuminating device to the plane of the microscope slide remains constant.

As mentioned above, the prior art described in U.S. Pat. No. 4,550,417 has the disadvantage that the microscope slide to be investigated is moved. The apparatus described above avoids this disadvantage in that the optical system comprising the line sensor, lens system and illuminating device is moved as a whole by means of the holder. Attaching all of the components to a rigid holder together ensures that the illumination and other optical conditions are the same for every line scanned on the surface to be investigated. The holder does not necessarily have to be guided by means of flexible spacer units, but rather the holder can be moved on a sled on ball bearings, for instance.

The invention also includes a method for optically investigating microscope slides in which an microscope slide is placed in an microscope slide holder,
  the microscope slide is illuminated by an illuminating device and its image is formed on a line sensor using a lens system from light passing through the microscope slide, whereby
  the illuminating device, lens system and line sensor are attached to a holder that, in turn, is attached to a support by means of at least one spacer unit, and the holder is moved over the surface of the microscope slide to be investigated basically vertically to the row of sensors in the line sensor by means of a drive and bending, tilting or pivoting the at least one spacer unit.

BRIEF DESCRIPTION OF THE DRAWINGS

The invention is explained in greater detail using the following figures.

DETAILED DESCRIPTION OF THE PREFERRED EMBODIMENTS

Figure 1:
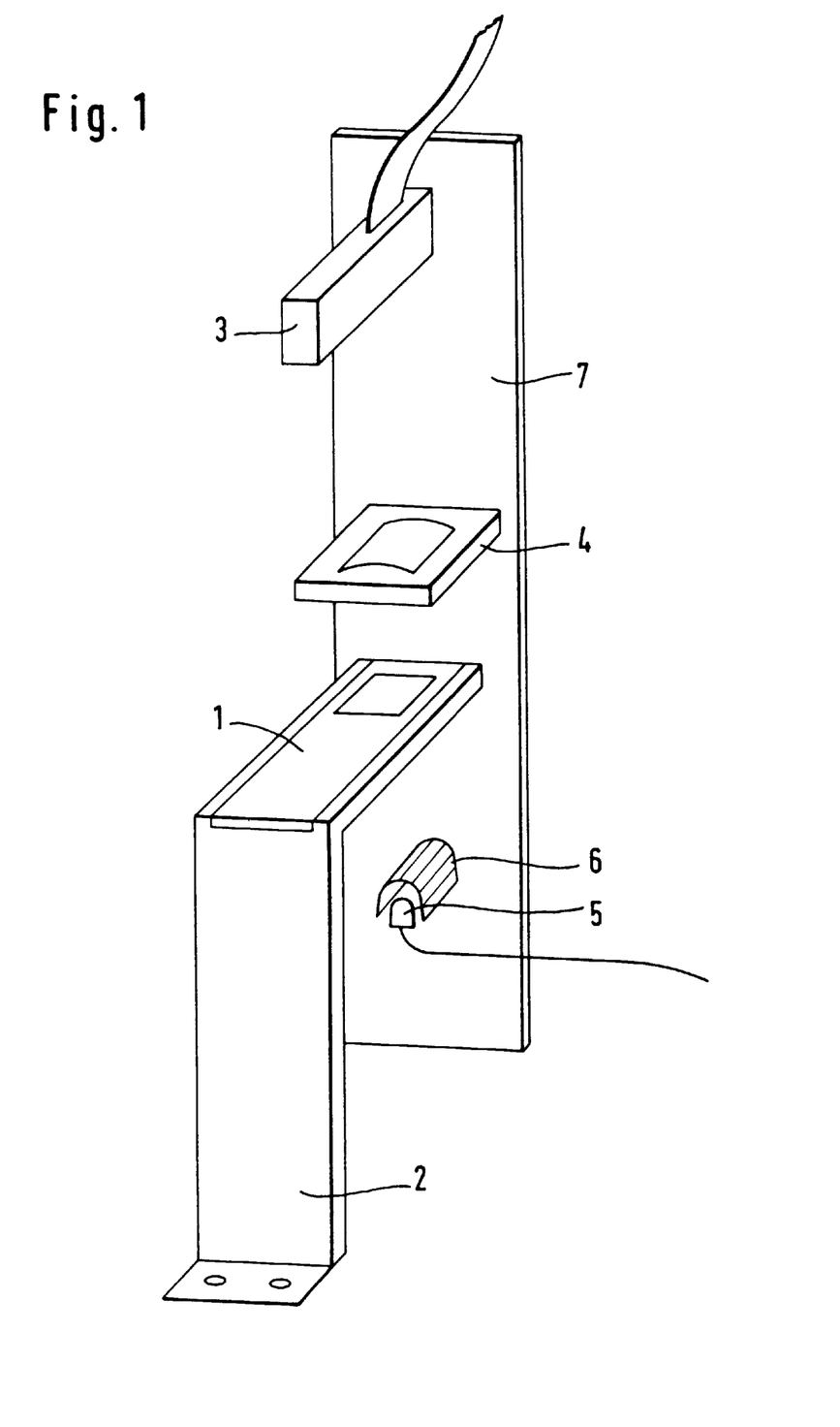
FIG. 1: Drawing of the optical device

The arrangement of the individual optical elements is shown in the drawing in FIG. 1. An microscope slide (1) is located in an microscope slide holder, which is attached to a support (2). A line sensor (3), lens system (4) and an array of light diodes (5) are attached to the holder (7). The light diodes (5) are covered by a curved matt screen (6). The light diodes have a wavelength of 592 nm (amber). The light that they emit, after passing through the focussing screen, illuminates the microscope slide (1) from below, and transmitted light forms an image on the line sensor (3) by means of the lens system (4). The lens system basically comprises an array of three cylindrical lenses that produce an enlargement factor of 2.97. The lens array forms a 3.7 μm-wide and 10 mm-long line image of the sample on the 11 μm-wide and 29.7 mm-long line sensor. The line sensor is a CCD sensor with 2700 pixels that are 11×11 μm in size. Its maximum sensitivity is achieved at a wavelength of 550 nm.

Figure 2:
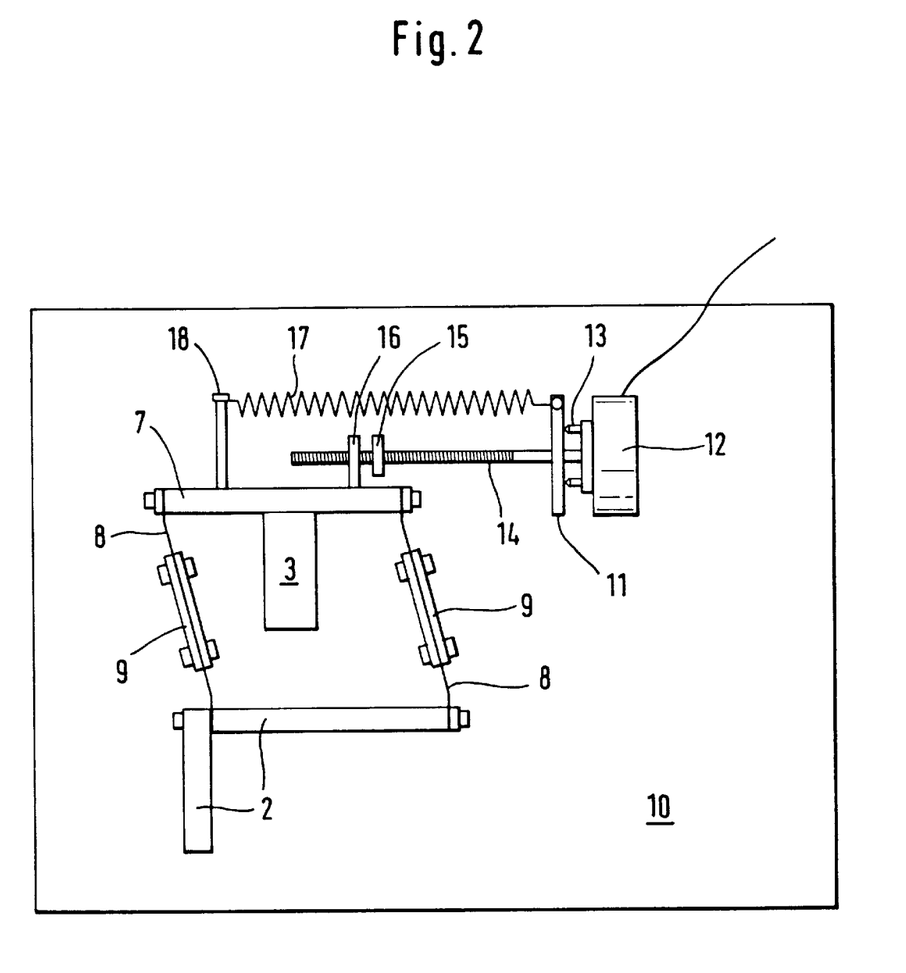
FIG. 2: View of a device

FIG. 2 shows a view of a device. The entire arrangement is mounted on a base plate (10). The support (2) is rigidly connected to the base plate (10). Two metal plates (8) made of chromium steel with a thickness of 0.05 mm are attached to the support. The metal plates (8) are the flexible spacer units. They are supported in the middle region by reinforcing elements (9) that are screwed into place. The holder (7) is connected to the support (2) by means of the spacer units (8). In this view one can see that the line sensor (3) is attached to the holder (7). A holding plate (16) that is positioned on the holder at a right angle is located on the side of the holder (7) facing away from the line sensor (3). The plate (15), containing a threaded nut, is attached to the holding plate (16) by means of a tip mount. The threaded rod (14), which is driven by the step motor (12), turns within the threaded nut. The step motor (12) is attached to the motor support (11) by means of a tip mount (13); the motor support (11) is rigidly connected with the base plate (10). To ensure that the desired high level of precision of the device is achieved, the play between the threaded nut and the threaded rod (14) is offset by applying tension to the holder (7) by means of the spring (17) and the spring holder (18). The spring (17) is located between the motor support (11) and the spring holder (18), and pulls the holder (7) in the direction of the motor.

In the design shown, the spacer units (8) have a width of 6 cm. The width of the holder is 5 cm, so that the optical arrangement is shaped like a tower with base surfaces that are almost square. In this case, a fine thread of M3×0.35 mm was selected for the threaded rod (14). The motor used has a torque of 250 g×cm, and a full revolution is divided into 96 individual steps. Each step of the step motor therefore covers a path of about 3.7 μm.

Figure 3:
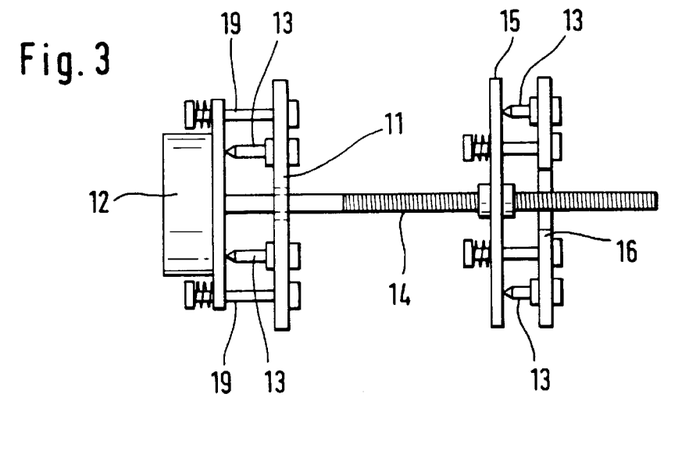
FIG. 3: Detailed drawing of the drive

FIG. 3 shows a detailed view of the drive. The motor (12) is connected with the motor support (11) by means of screws (19) with a spring base. The screws (13) are used to tip-mount the motor. The threaded rod (14) turns within a threaded nut that is located in the plate (15). The plate (15) is connected with the holding plate (16) by means of spring-based screws. The plate (15) is also tip-mounted by means of screws (13).

Figure 4:
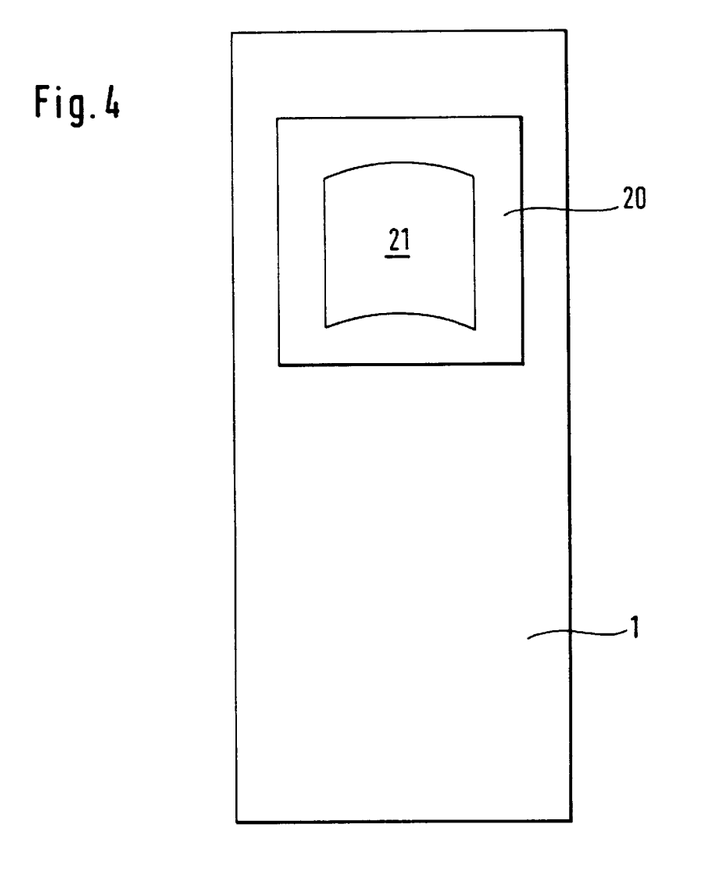
FIG. 4: Microscope slide showing the surface area investigated

FIG. 4 shows a top view of an microscope slide (1) with an evaluation chamber (20). The surface (21) depicts the shape of the area of the evaluation chamber scanned by the device. One can see that the sensor moves like a windshield wiper, thereby scanning a corresponding area. In the actual case that has been realized, the scanned area is 10×10 mm.

Figure 5:
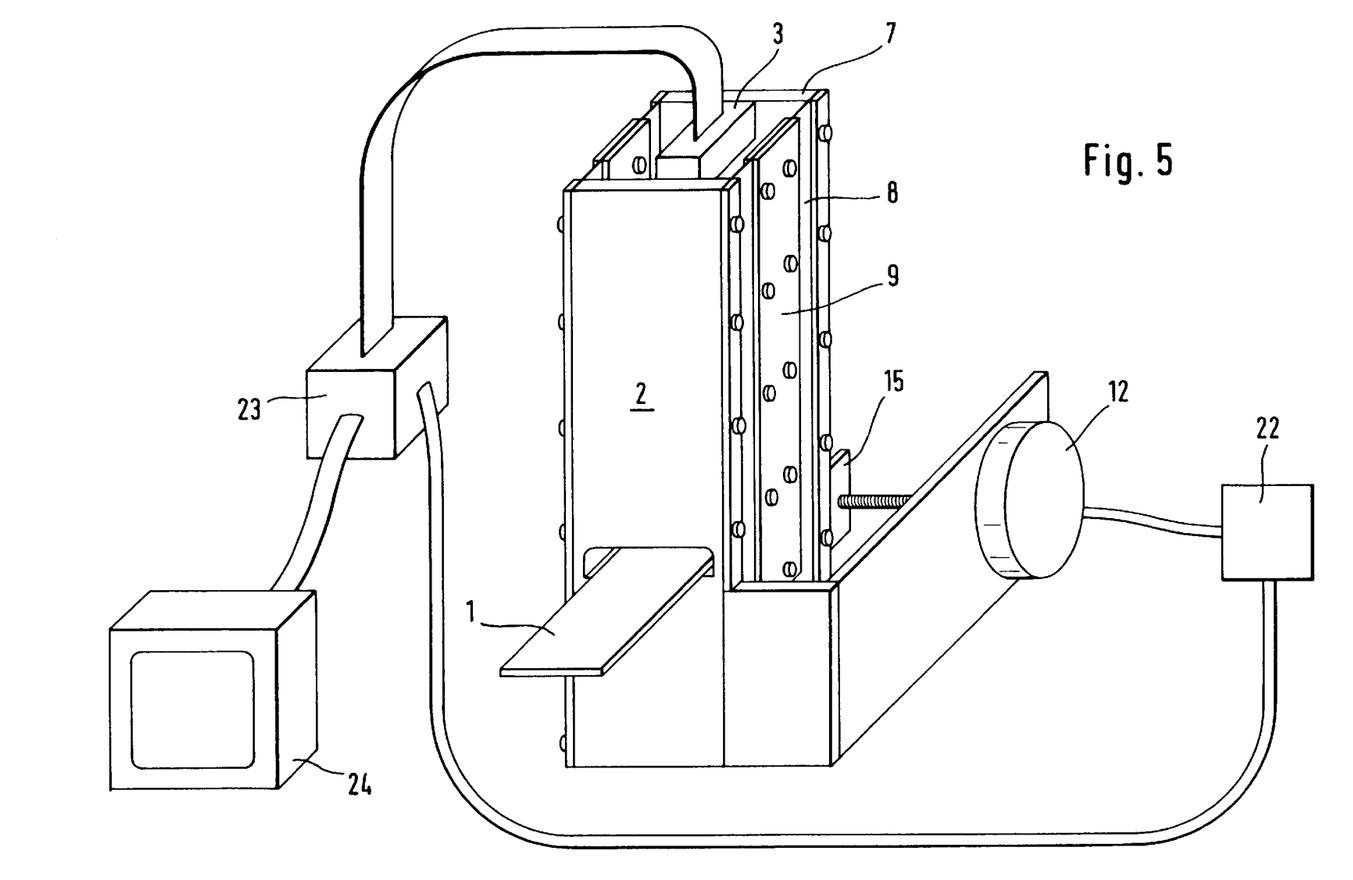
FIG. 5: Three-dimensional drawing of the device with drive and evaluation unit

FIG. 5 shows a three-dimensional drawing of a device for use in the investigation of microscope slides. The microscope slide (1) is inserted into a microscope slide holder (not shown) through an opening in the support (2). The spacer units (8) are attached to the side of the support. The spacer unit is supported by a reinforcing element (9). The spacer units (8) carry the holder (7) to which the line sensor (3) is attached. Signals delivered by the line sensor (3) are converted into digital values and then forwarded to the data processing and control device (23) by means of a data cable. The results of the evaluation or a representation of the scanned surfaces are displayed on a monitor (24) by the data processing device (23). As an option, the data processing device is connected to the motor control (22).

Reference Numeral List 1) microscope slide
2) support
3) line sensor
4) lens system
5) light diode
6) matt screen
7) holder
8) spacer unit
9) reinforcing element
10) base plate
11) motor support
12) motor
13) tip mount
14) threaded rod
15) plate with nut
16) holding plate
17) spring
18) spring holder
19) spring-based screw
20) measuring chamber
21) test area
22) motor control
23) data processing and control device
24) monitor

What is claimed is:

1. A device for optical investigation of a microscope slide, said device comprising:
    a support;
    a microscope slide holder fixedly attached to said support;
    a holder unit attached to said support with at least one spacer unit, said at least one spacer unit enabling relative movement between the holder unit and the support;
    a line sensor attached to said holder unit, said line sensor comprising a plurality of sensors arranged in a row;
    an illuminating device for illuminating a microscope slide disposed on said microscope slide holder;
    a lens system attached to said holder unit, said lens system generating an image on said line sensor of at least a part of the microscope slide; and
    a drive for moving the holder unit substantially vertically relative to the sensors of the line sensor.

2. A device as recited in claim 1, wherein said drive moves the holder unit substantially vertically in a scanning motion, said scanning motion deviating from vertical by an amount defined by a relative movement path provided by the spacer unit.

3. A device for optical investigation of a microscope slide, said device comprising:
    a support means for supporting device elements thereupon;
    microscope slide holder means fixedly attached to said support means, said microscope slide holder means for holding a microscope slide therein;
    holder means attached to said support means with at least one spacer means, said holder means for holding optical elements thereupon and said spacer means for enabling relative movement between the holder means and the support means;

line sensor means attached to said holder unit, said line sensor means for sensing optical images thereupon;

illuminating means for illuminating a microscope slide disposed on said microscope slide holder means;

lens means attached to said holder means, said lens means for generating the optical image on the line sensor of at least a part of the microscope slide; and drive means for moving the holder means substantially vertically relative to the line sensor means.

4. A device as recited in claim 3, wherein said drive means moves the holder means substantially vertically in a scanning motion, said scanning motion deviating from vertical by an amount defined by a relative movement path provided by the spacer means.

5. A device for optical investigation of surfaces, said device comprising:

a support;

a holder unit being attached to said support by a spacer unit, said spacer unit enabling relative movement between the holder unit and the support;

a line sensor having a plurality of sensors arranged in a row, said line sensor being attached to said holder unit;

a lens system attached to said holder unit, said lens system for providing an image of a surface under investigation on the line sensor; and a drive unit for driving the holder unit relative to the support, said holder unit being moved in a substantially vertical direction with respect to the plurality of sensors of the line sensor.

6. A device as recited in claim 5, wherein said drive unit drives the holder in the substantially vertical direction in a curved scanning motion.

7. A device for optical investigation of microscope slides, said device comprising:

a support having a microscope slide holder attached thereto;

a holder unit being movable relative to said support, said holder unit including a line sensor, a lens system, and an illuminating device thereupon;

a drive unit for driving the holder unit, said drive unit driving said holder unit such that a distance between elements attached to the holder unit and a plane of a microscope slide in said microscope slide holder remains substantially constant.

8. A device as recited in claim 7, wherein said drive unit drives the holder unit in a scanning motion.

9. A device for optical investigation of a microscope slide, said device comprising:

a support having a microscope slide holder attached thereto, said microscope slide holder being attached to said support by at least one spacer unit;

a line sensor attached to the support, said line sensor including a plurality of sensors arranged in a row;

a lens system attached to said support, said lens system generating an image of a microscope slide in said microscope slide holder on the line sensor;

an illuminating device for illuminating the microscope slide; and a drive unit for moving the microscope slide holder substantially vertically relative to the plurality of sensors in the line sensor.

10. A device as recited in claim 9, wherein said drive unit moves the microscope slide substantially vertically in a scanning motion defined by relative movement permitted by a configuration of the support, the microscope slide holder, and the at least one spacer unit.

11. A device as recited in claim 1, wherein said spacer unit comprises a flexible member which enables relative movement between the support and the holder unit.

12. A device as recited in claim 3, wherein said spacer means comprises a flexible member which enables relative movement between the support means and the holder means.

13. A device as recited in claim 5, wherein said spacer unit comprises a flexible member which enables the relative movement between the holder unit and the support.

14. A device as recited in claim 9, wherein said spacer unit comprises a flexible member enabling relative movement between the microscope slide holder and the support.

15. A device as recited in claim 5, said device further comprising an illuminating unit for illuminating the surface under investigation.

16. A device as recited in claim 5, wherein said support includes elements for placing the support on the surface under investigation.

17. A device as recited in claim 1, wherein said illuminating device is attached to said holder unit.

18. A device as recited in claim 7, wherein said illuminating device is attached to said holder unit.

19. A device as recited in claim 1, wherein said illuminating device comprises a plurality of monochromatic light diodes arranged in a row.

20. A device as recited in claim 3, wherein said illuminating means comprises a plurality of monochromatic light diodes arranged in a row.

21. A device as recited in claim 7, wherein said illuminating device comprises a plurality of monochromatic light diodes arranged in a row.

22. A device as recited in claim 9, wherein said illuminating device comprises a plurality of monochromatic light diodes arranged in a row.

23. A device as recited in claim 1, wherein said illuminating device comprises at least two differently colored light diodes, said light diodes being configured to be alternatingly illuminated.

24. A device as recited in claim 3, wherein said illuminating means comprises at least two differently colored light diodes, said light diodes being configured to be alternatingly illuminated.

25. A device as recited in claim 7, wherein said illuminating device comprises at least two differently colored light diodes, said light diodes being configured to be alternatingly illuminated.

26. A device as recited in claim 9, wherein said illuminating device comprises at least two differently colored light diodes, said light diodes being configured to be alternatingly illuminated.

27. A device as recited in claim 19, wherein said illuminating device comprises a mat screen, wherein light emitted by the light diodes is irradiated onto the mat screen before the light impinges upon the microscope slide.

28. A device as recited in claim 20, wherein said illuminating means comprises a mat screen, wherein light emitted by the light diodes is irradiated onto the mat screen before the light impinges upon the microscope slide.

29. A device as recited in claim 22, wherein said illuminating device comprises a mat screen, wherein light emitted by the light diodes is irradiated onto the mat screen before the light impinges upon the microscope slide.

30. A device as recited in claim 23, wherein said illuminating device further comprises a mat screen onto which light emitted from the light diodes is irradiated prior to being irradiated onto the microscope slide.

31. A device as recited in claim 24, wherein said illuminating means further comprises a mat screen onto which light emitted from the light diodes is irradiated prior to being irradiated onto the microscope slide.

32. A device as recited in claim 25, wherein said illuminating device further comprises a mat screen onto which light emitted from the light diodes is irradiated prior to being irradiated onto the microscope slide.

33. A device as recited in claim 26, wherein said illuminating device further comprises a mat screen onto which light emitted from the light diodes is irradiated prior to being irradiated onto the microscope slide.

34. A device as recited in claim 1, wherein the illuminating device, the lens system, and the line sensor are configured with the microscope slide to perform transmitted-light microscopy.

35. A device as recited in claim 9, wherein the illuminating device, the lens system, and the line sensor are configured with the microscope slide to perform transmitted-light microscopy.

36. A device as recited in claim 1, wherein said holder unit is attached to said support with at least two spacer units, each of said at least two spacer units being separated from each other.

37. A device as recited in claim 9, wherein said holder unit is attached to said support with at least two spacer units, each of said at least two spacer units being separated from each other.

38. A device as recited in claim 1, wherein said drive comprises a threaded nut being attached to said holder unit, a threaded rod received in said threaded nut, said threaded rod being driven by a motor.

39. A device as recited in claim 9, wherein said drive comprises a threaded nut being attached to said holder unit, a threaded rod received in said threaded nut, said threaded rod being driven by a motor.

40. A device according to claim 38, further comprising a plate attached to the holder unit, wherein said threaded nut is attached to said plate.

41. A device according to claim 39, further comprising a plate attached to the holder unit, wherein said threaded nut is attached to said plate.

42. A device as recited in claim 1, wherein said spacer unit is a flexible spacer unit having an elastic force of 5–100 g/mm.

43. A device as recited in claim 3, wherein said spacer means is a flexible spacer means having an elastic force of 5–100 g/mm.

44. A device as recited in claim 5, wherein said spacer unit is a flexible spacer unit having an elastic force of 5–100 g/mm.

45. A device as recited in claim 9, wherein said spacer unit is a flexible spacer unit having an elastic force of 5–100 g/mm.

46. A device as recited in claim 1, wherein said drive comprises a drive motor having a torque between 100 and 500 g/cm.

47. A device as recited in claim 9, wherein said drive comprises a drive motor having a torque between 100 and 500 g/cm.

48. A method for optical investigation of microscope slides, said method comprising the steps of:

placing a microscope slide in a microscope slide holder;

illuminating the microscope slide with an illuminating device, wherein light passes through the microscope slide;

focusing the light passed through the microscope slide through a lens system, focused light from the lens system thereby forming an image on a line sensor; and moving the illuminating device, the lens system, and the line sensor relative to a surface of the microscope slide, said moving step moving sensors in the line sensor substantially vertically relative to the surface of the microscope slide, and wherein the illuminating device, lens system, and line sensor are configured on a holder which is moved relative to a support supporting the microscope slide, said relative movement being enabled by spacer elements which are configured to connect the holder to the support and enable relative movement therebetween.

49. A method as recited in claim 48, wherein said step of moving the illuminating device comprises moving the sensors in the line sensor substantially vertically in a scanning motion relative to the surface of the microscope slide, said scanning motion including a non-linear movement.

* * * * *